United States Patent
Scheel-Krüger et al.

(10) Patent No.: US 9,457,018 B2
(45) Date of Patent: Oct. 4, 2016

(54) METHOD FOR COMBATING ADVERSE EFFECTS ARISING FROM ANTIPSYCHOTIC TREATMENT

(75) Inventors: Jørgen Scheel-Krüger, Glostrup (DK); Henrik Björk Hansen, København N (DK)

(73) Assignee: Saniona A/S, Ballerup (DK)

( * ) Notice: Subject to any disclaimer, the term of this patent is extended or adjusted under 35 U.S.C. 154(b) by 78 days.

(21) Appl. No.: 13/061,853

(22) PCT Filed: Sep. 2, 2009

(86) PCT No.: PCT/EP2009/061332
§ 371 (c)(1),
(2), (4) Date: May 26, 2011

(87) PCT Pub. No.: WO2010/026154
PCT Pub. Date: Mar. 11, 2010

(65) Prior Publication Data
US 2012/0202796 A1    Aug. 9, 2012

Related U.S. Application Data

(60) Provisional application No. 61/094,426, filed on Sep. 5, 2008.

(30) Foreign Application Priority Data

Sep. 4, 2008    (DK) .................. 2008 01225

(51) Int. Cl.
*A61K 31/4418* (2006.01)
*C07D 211/22* (2006.01)
*A61K 31/46* (2006.01)
*A61K 31/5513* (2006.01)

(52) U.S. Cl.
CPC ........... *A61K 31/46* (2013.01); *A61K 31/5513* (2013.01)

(58) Field of Classification Search
CPC ................ A61K 31/4418; C07D 211/22
USPC ................... 548/400; 546/194; 514/317
See application file for complete search history.

(56) References Cited

U.S. PATENT DOCUMENTS

| | | |
|---|---|---|
| 2007/0078162 A1 | 4/2007 | Buntinx |
| 2008/0153888 A1 | 6/2008 | Leonardi et al. |
| 2010/0234349 A1* | 9/2010 | Olsen et al. ............. 514/211.13 |

FOREIGN PATENT DOCUMENTS

| | | |
|---|---|---|
| EP | 1 541 197 A1 | 6/2005 |
| EP | 1541197 * | 6/2005 |
| WO | WO 2008/077599 A1 | 7/2008 |

OTHER PUBLICATIONS

Neurosearch reference Jul. 8, 2008 http://www.evaluategroup.com/Universal/View.aspx?type=Story&id=16000.*
Eder, Am. J. Psychiatry, vol. 158, Issue 10, Oct. 2001, p. 1719-1722.*
Astrup, A. et al. "The efficacy and safety of tesofensine for wight loss in obese subjects. A 24-week randomised, double-blind, placebo-controlled Danish multi-centre trial", Intl. J. of Obesity, vol. 32, No. Suppl. 1. May 1, 2008, pp. S23. XP009124816.
Baptista, T. et al. "The Metabolic Syndrome During Atypical Antipsychotic Drug Treatment: Mechanisms and Management", Metabolic Syndrome and Related Disorders, vol. 2. No. 4. Oct. 2004. pp. 290-307. XP009124809.
Henderson, D. et al. "A double-blind, placebo-controlled trial of sibutramine for olanzapine-associated weight gain.", Am. J. Psychiatry vol. 162, No. 5, May 2005. pp. 954-962. XP-002552520.
International Search Report, dated Nov. 6, 2009, issued in PCT/EP2009/061332.
Milano et al., "Appropriate Intervention Strategies for Weight Gain Induced by Olanzapine: A Randomized Controlled Study", Advances in Therapy, Jan./Feb. 2007, vol. 24, No. 1, 123-134.
Assuncao et al., "Weight gain management in patients with schizophrenia during treatment with olanzapine in association with nizatidine", Rev. Bras. Psiquiatar., 2006, 28(4), 270-276.
Bustillo et al., "Treatment of Weight Gain with Fluoxetine in Olanzapine-Treated Schizophrenic Outpatients", Neuropsychopharmacology, 2003, 28, 527-529.
Ball et al., "Placebo-Controlled Trial of Atomoxetine for Weight Reduction in People with Schizophrenia Treated with Clozapine or Olanzapine", Clinical Schizophrenia & Related Psychoses, Apr. 2011, 17-25.
Baptista et al., "Pharmacological Management of Atypical Antipsychotic-Induced Weight Gain", CNS Drugs, 2008, 22(6), 477-495.

* cited by examiner

*Primary Examiner* — Yong Chu
*Assistant Examiner* — Sonya Wright
(74) *Attorney, Agent, or Firm* — Baker & Hostetler LLP

(57) ABSTRACT

This invention relates to a method for combating adverse effects arising from antipsychotic treatment. The invention furthermore relates to novel pharmaceutical compositions comprising a therapeutically effective combination of a compound of formula I and an antipsychotic drug.

11 Claims, 2 Drawing Sheets

METHOD FOR COMBATING ADVERSE EFFECTS ARISING FROM ANTIPSYCHOTIC TREATMENT

This application is the National Phase of PCT/EP2009/061332 filed on Sep. 2, 2009, which claims priority under 35 U.S.C. 119(e) to U.S. Provisional Application No. 61/094,426 filed on Sep. 5, 2008 and under 35 U.S.C. 119(a) to Patent Application No. PA 2008 01225 filed in Denmark on Sep. 4, 2008, all of which are hereby expressly incorporated by reference into the present application.

TECHNICAL FIELD

This invention relates to a method for combating adverse effects arising from antipsychotic treatment. The invention furthermore relates to novel pharmaceutical compositions comprising a therapeutically effective combination of a compound of formula I and an antipsychotic drug.

BACKGROUND ART

Olanzapine is an efficacious antipsychotic medication, but like other antipsychotic drugs currently used, olanzapine can induce significant weight gain and other adverse effects, Weight gain is among the most frequent adverse effects and increased appetite is also relatively common.

Thus there is impetus for creating new and alternative treatments for controlling i.a. weight gain associated with antipsychotic treatment.

SUMMARY OF THE INVENTION

In its first aspect the invention provides a method of treatment, prevention or alleviation of an adverse effect arising from antipsychotic treatment of a living animal body, including a human, which method comprises the step of administering to such a living animal body in need thereof, a therapeutically effective amount of a compound of formula I, any of its stereoisomers or any mixture of its stereoisomers, or a pharmaceutically acceptable salt thereof.

In another aspect the invention provides a compound of formula I, any of its stereoisomers or any mixture of its stereoisomers, or a pharmaceutically acceptable salt thereof; for use in the treatment, prevention or alleviation of an adverse effect arising from antipsychotic treatment of a mammal, including a human.

In a third aspect the invention provides the use of a compound of formula I, any of its stereoisomers or any mixture of its stereoisomers, or a pharmaceutically acceptable salt thereof; for the manufacture of a medicament for the treatment, prevention or alleviation of an adverse effect arising from antipsychotic treatment.

In a fourth aspect the invention provides a pharmaceutical composition comprising a therapeutically effective amount of a compound of formula I, any of its stereoisomers or any mixture of its stereoisomers, or a pharmaceutically acceptable salt thereof and an antipsychotic drug or a pharmaceutically acceptable salt thereof, together with one or more adjuvants, excipients, carriers and/or diluents.

In further aspect the invention relates to the use of a combination of a compound of formula I, any of its stereoisomers or any mixture of its stereoisomers, or a pharmaceutically acceptable salt thereof and an antipsychotic drug or a pharmaceutically acceptable salt thereof, for the manufacture of a medicament for the treatment, prevention or alleviation of an adverse effect arising from antipsychotic treatment of a mammal, including a human.

In still further aspect the invention provides a kit of parts comprising at least two separate unit dosage forms (A) and (B), wherein (A) comprises a compound of formula I, any of its stereoisomers or any mixture of its stereoisomers, or a pharmaceutically acceptable salt thereof; and (B) comprises an antipsychotic drug or a pharmaceutically acceptable salt thereof; and optionally (C) instructions for the simultaneous, sequential or separate administration of the compound of (A) and the antipsychotic drug of (B) to a patient in need thereof.

In a further aspect the invention provides a method of treatment, prevention or alleviation of an adverse effect arising from antipsychotic treatment of a living animal body, including a human, which method comprises the step of administering to such a living animal body in need thereof, a therapeutically effective amount of a compound of formula I, any of its stereoisomers or any mixture of its stereoisomers, or a pharmaceutically acceptable salt thereof; and an antipsychotic drug or a pharmaceutically acceptable salt thereof.

Other objects of the invention will be apparent to the person skilled in the art from the following detailed description and examples.

DETAILED DISCLOSURE OF THE INVENTION

In its first aspect the invention provides a method of treatment, prevention or alleviation of an adverse effect arising from antipsychotic treatment of a living animal body, including a human, which method comprises the step of administering to such a living animal body in need thereof, a therapeutically effective amount of a compound of formula I

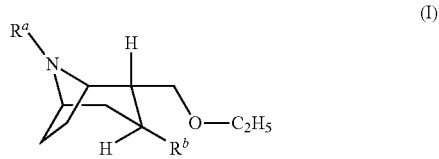

(I)

wherein $R^a$ represents hydrogen or alkyl; and $R^b$ represents a dihalophenyl group;

any of its stereoisomers or any mixture of its stereoisomers, or a pharmaceutically acceptable salt thereof.

Compounds of Formula I

The compounds of formula I for use according to the invention are described in WO 97/30997 (NeuroSearch A/S). The compounds may be prepared by conventional methods for chemical synthesis, e.g. those described in WO 97/30997 and WO 2005/073228.

In one embodiment of the compound of formula I, $R^a$ represents hydrogen or methyl. In a special embodiment, $R^a$ represents hydrogen. In a further embodiment, $R^a$ represents methyl.

In a further embodiment of the compounds of formula I, $R^b$ represents dichlorophenyl. In a special embodiment, $R^b$ represents 3,4-dichlorophenyl.

In a still further embodiment, the compound of formula I is tesofensine[(1R,2R,3S,5S)-3-(3,4-dichlorophenyl)-2-(ethoxymethyl)-8-methyl-8-azabicyclo[3.2.1]octane]; or (1R,2R,3S,5S)-3-(3,4-dichlorophenyl)-2-(ethoxymethyl)-8-azabicyclo[3.2.1]octane;

or a pharmaceutically acceptable salt thereof.

In a special embodiment, the compound of formula I is tesofensine or a pharmaceutically acceptable salt thereof. In a further special embodiment, the compound of formula I is the citrate salt of tesofensine.

Definition of Substituents

In the context of this invention halo represents fluoro, chloro, bromo or iodo.

In the context of this invention an alkyl group means a straight chain or branched chain of one to six carbon atoms, including but not limited to, methyl, ethyl, propyl, isopropyl, butyl, isobutyl, t-butyl, pentyl, and hexyl; methyl, ethyl, propyl and isopropyl are preferred groups.

Steric Isomers

It will be appreciated by those skilled in the art that the compounds of formula I may exist in different stereoisomeric forms—including enantiomers, diastereomers and cis-trans-isomers.

The invention includes all such isomers and any mixtures thereof including racemic mixtures.

Antipsychotic Drugs

The antipsychotic drug for use according to the invention is known in the art. Preferably, the antipsychotic drug is an atypical antipsychotic drug, which drugs are known in the art and may be commercially available under different brand names, or may be obtained as described in the literature:

In one embodiment, the antipsychotic drug is selected from the group consisting of amisulpride, aripiprazole, asenapine, bifeprunox, clozapine, iloperidone, melperone, olanzapine, paliperidone, quetiapine, risperidone, sertindole, ziprasidone, zotepine and pharmaceutically acceptable salts thereof.

In a further embodiment, the antipsychotic drug is selected from the group consisting of clozapine, olanzapine, quetiapine, risperidone, zotepine and pharmaceutically acceptable salts thereof.

In a still further embodiment, the antipsychotic drug is olanzapine.

Combinations of Compounds of Formula I and Antipsychotic Drug Treatments

In a special embodiment of the invention, the compound of formula I is tesofensine or a pharmaceutically acceptable salt thereof and the antipsychotic drug is selected from the group consisting of: amisulpride, aripiprazole, asenapine, bifeprunox, clozapine, iloperidone, melperone, olanzapine, paliperidone, quetiapine, risperidone, sertindole, ziprasidone, zotepine, and pharmaceutically acceptable salts thereof.

In a further special embodiment, the compound of formula I is tesofensine or a pharmaceutically acceptable salt thereof and the antipsychotic drug is amisulpride or a pharmaceutically acceptable salt thereof.

In a still further special embodiment, the compound of formula I is tesofensine or a pharmaceutically acceptable salt thereof and the antipsychotic drug is aripiprazole or a pharmaceutically acceptable salt thereof.

In a further special embodiment, the compound of formula I is tesofensine or a pharmaceutically acceptable salt thereof and the antipsychotic drug is asenapine or a pharmaceutically acceptable salt thereof.

In a still further special embodiment, the compound of formula I is tesofensine or a pharmaceutically acceptable salt thereof and the antipsychotic drug is bifeprunox or a pharmaceutically acceptable salt thereof.

In a further special embodiment, the compound of formula I is tesofensine or a pharmaceutically acceptable salt thereof and the antipsychotic drug is clozapine or a pharmaceutically acceptable salt thereof.

In a still further special embodiment, the compound of formula I is tesofensine or a pharmaceutically acceptable salt thereof and the antipsychotic drug is iloperidone or a pharmaceutically acceptable salt thereof.

In a further special embodiment, the compound of formula I is tesofensine or a pharmaceutically acceptable salt thereof and the antipsychotic drug is melperone or a pharmaceutically acceptable salt thereof.

In a still further special embodiment, the compound of formula I is tesofensine or a pharmaceutically acceptable salt thereof and the antipsychotic drug is olanzapine or a pharmaceutically acceptable salt thereof.

In a further special embodiment, the compound of formula I is tesofensine or a pharmaceutically acceptable salt thereof and the antipsychotic drug is paliperidone or a pharmaceutically acceptable salt thereof.

In a still further special embodiment, the compound of formula I is tesofensine or a pharmaceutically acceptable salt thereof and the antipsychotic drug is quetiapine or a pharmaceutically acceptable salt thereof.

In a further special embodiment, the compound of formula I is tesofensine or a pharmaceutically acceptable salt thereof and the antipsychotic drug is risperidone or a pharmaceutically acceptable salt thereof.

In a still further special embodiment, the compound of formula I is tesofensine or a pharmaceutically acceptable salt thereof and the antipsychotic drug is sertindole or a pharmaceutically acceptable salt thereof.

In a further special embodiment, the compound of formula I is tesofensine or a pharmaceutically acceptable salt thereof and the antipsychotic drug is ziprasidone or a pharmaceutically acceptable salt thereof.

In a still further special embodiment, the compound of formula I is tesofensine or a pharmaceutically acceptable salt thereof and the antipsychotic drug is zotepine or a pharmaceutically acceptable salt thereof.

Pharmaceutically Acceptable Salts

The active compounds for use according to the invention may be provided in any form suitable for the intended administration. Suitable forms include pharmaceutically (i.e. physiologically) acceptable salts, and pre- or prodrug forms of the compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound for use according to the invention include examples of suitable prodrugs of the substances for use according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compounds for use according to the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Biological Activity

The disease, disorder or condition to be treated, prevented or alleviated according to the present invention is an adverse effects arising from antipsychotic treatment.

In one embodiment, the disease, disorder or condition to be treated, prevented or alleviated is an adverse effects arising from treatment with antipsychotic drugs.

In a further embodiment, the disease, disorder or condition to be treated, prevented or alleviated is an adverse effects arising from treatment with an antipsychotic drug selected from the group consisting of amisulpride, aripiprazole, asenapine, bifeprunox, clozapine, iloperidone, melperone, olanzapine, paliperidone, quetiapine, risperidone, sertindole, ziprasidone, zotepine and pharmaceutically acceptable salts thereof.

In a further embodiment, the disease, disorder or condition to be treated, prevented or alleviated is an adverse effects arising from treatment with an antipsychotic drug selected from the group consisting of clozapine, olanzapine, quetiapine, risperidone, zotepine and pharmaceutically acceptable salts thereof.

In a still further embodiment, the disease, disorder or condition to be treated, prevented or alleviated is an adverse effects arising from treatment with olanzapine or a pharmaceutically acceptable salt thereof.

In a further embodiment, the disease, disorder or condition to be treated, prevented or alleviated is selected from the group of weight gain, obesity, dyslipidemia, impaired glucose tolerance, hyperglycemia, decreased insulin sensitivity and impaired lipid metabolism.

In still a further embodiment, the disease, disorder or condition to be treated, prevented or alleviated is weight gain. In a special embodiment, the disease, disorder or condition to be treated, prevented or alleviated is weight gain arising from treatment with olanzapine or a pharmaceutically acceptable salt thereof.

In a further embodiment, the disease, disorder or condition to be treated, prevented or alleviated is obesity. In a special embodiment, the disease, disorder or condition to be treated, prevented or alleviated is obesity arising from treatment with olanzapine or a pharmaceutically acceptable salt thereof.

In still a further embodiment, the disease, disorder or condition to be treated, prevented or alleviated is dyslipidemia. In a special embodiment, the disease, disorder or condition to be treated, prevented or alleviated is dyslipidemia arising from treatment with olanzapine or a pharmaceutically acceptable salt thereof.

In a further embodiment, the disease, disorder or condition to be treated, prevented or alleviated is impaired glucose tolerance. In a special embodiment, the disease, disorder or condition to be treated, prevented or alleviated is impaired glucose tolerance arising from treatment with olanzapine or a pharmaceutically acceptable salt thereof.

In still a further embodiment, the disease, disorder or condition to be treated, prevented or alleviated is hyperglycemia. In a special embodiment, the disease, disorder or condition to be treated, prevented or alleviated is hyperglycemia arising from treatment with olanzapine or a pharmaceutically acceptable salt thereof.

In still a further embodiment, the disease, disorder or condition to be treated, prevented or alleviated is decreased insulin sensitivity. In a special embodiment, the disease, disorder or condition to be treated, prevented or alleviated is decreased insulin sensitivity arising from treatment with olanzapine or a pharmaceutically acceptable salt thereof.

In still a further embodiment, the disease, disorder or condition to be treated, prevented or alleviated is impaired lipid metabolism. In a special embodiment, the disease, disorder or condition to be treated, prevented or alleviated is impaired lipid metabolism arising from treatment with olanzapine or a pharmaceutically acceptable salt thereof.

Biological Activity of the Combination

In a further embodiment—in addition to the above—the disease, disorder or condition to be treated, prevented or alleviated with the combination according to the present invention is selected from schizophrenia, bipolar disorder, bipolar I disorder and bipolar II disorder.

Pharmaceutical Compositions

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In a preferred embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in drage, in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

Dosages

The actual dosage of each of the active ingredients depends on the nature and severity of the disease being treated, the exact mode of administration, form of administration and is within the discretion of the physician, and may be varied by titration of the dosage to the particular circumstances of this invention to produce the desired therapeutic effect. However, the below dosages for the compound of formula I and the antipsychotic drug are considered suitable.

The dosage of the compound of formula I is determined as the API (Active Pharmaceutical Ingredient), i.e. calculated as the free base. A daily dosage in the range of about 0.1-2 mg API daily, preferably of about 0.25-1 mg API daily, especially 0.25, 0.5 or 1.0 mg API daily, is suitable for therapeutic treatments. The daily dosage of the compound of formula I may be administered in one or several doses, such as two, per day. In one embodiment, the daily dosage is administered in one dose.

The daily dosage of the antipsychotic drug is presently contemplated to be in the range of about 0.1-500 mg of active ingredient depending on the actual compound. More specific dosage intervals may be in the range of about 0.1-2 mg, about 1-10 mg, about 10-50 mg, about 25-100 mg, about 50-200 mg and about 100-500 mg daily. The daily dosage of the antipsychotic drug may be administered in one or several doses, such as two, per day. In one embodiment, the daily dosage is administered in one dose.

Pharmaceutical Kits of Parts

According to the invention there is also provided a kit of parts comprising at least two separate unit dosage forms (A) and (B):

(A) a compound of formula I

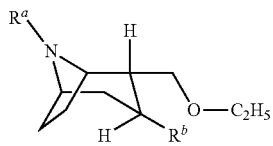

(I)

wherein
$R^a$ represents hydrogen or alkyl; and
$R^b$ represents a dihalophenyl group;
any of its stereoisomers or any mixture of its stereoisomers, or a pharmaceutically acceptable salt thereof; and
(B) an antipsychotic drug;
or a pharmaceutically acceptable salt thereof; and optionally
(C) instructions for the simultaneous, sequential or separate administration of the compound of (A) and the antipsychotic drug of (B) to a patient in need thereof.

The compound of formula I for use according to the invention and the antipsychotic drug for use according to the invention may preferably be provided in a form that is suitable for administration in conjunction with the other. This is intended to include instances where one or the other of two formulations may be administered (optionally repeatedly) prior to, after, and/or at the same time as administration with the other component.

Also, the compound of formula I for use according to the invention and the antipsychotic drug for use according to the invention may be administered in a combined form, or separately or separately and sequentially, wherein the sequential administration is close in time or remote in time. This may in particular include that two formulations are administered (optionally repeatedly) sufficiently closely in time for there to be a beneficial effect for the patient, that is greater over the course of the treatment of the relevant condition than if either of the two formulations are administered (optionally repeatedly) alone, in the absence of the other formulation, over the same course of treatment. Determination of whether a combination provides a greater beneficial effect in respect of, and over the course of treatment of, a particular condition, will depend upon the condition to be treated or prevented, but may be achieved routinely by the person skilled in the art.

When used in this context, the terms "administered simultaneously" and "administered at the same time as" include that individual doses of the compound of formula I and the antipsychotic drug are administered within 48 hours, e.g. 24 hours, of each other.

Bringing the two components into association with each other, includes that components (A) and (B) may be provided as separate formulations (i.e. independently of one another), which are subsequently brought together for use in conjunction with each other in combination therapy; or packaged and presented together as separate components of a "combination pack" for use in conjunction with each other in combination therapy.

Methods of Therapy

The preferred indications contemplated according to the invention are those stated above.

When administered in combination with further compounds known in the art for treatment of the diseases, the dose regimen may be reduced.

BRIEF DESCRIPTION OF THE DRAWINGS

The present invention is further illustrated by reference to the accompanying drawing, in which.

EXAMPLES

The invention is further illustrated with reference to the following examples, which are not intended to be in any way limiting to the scope of the invention as claimed.

Example 1

Figure 1:
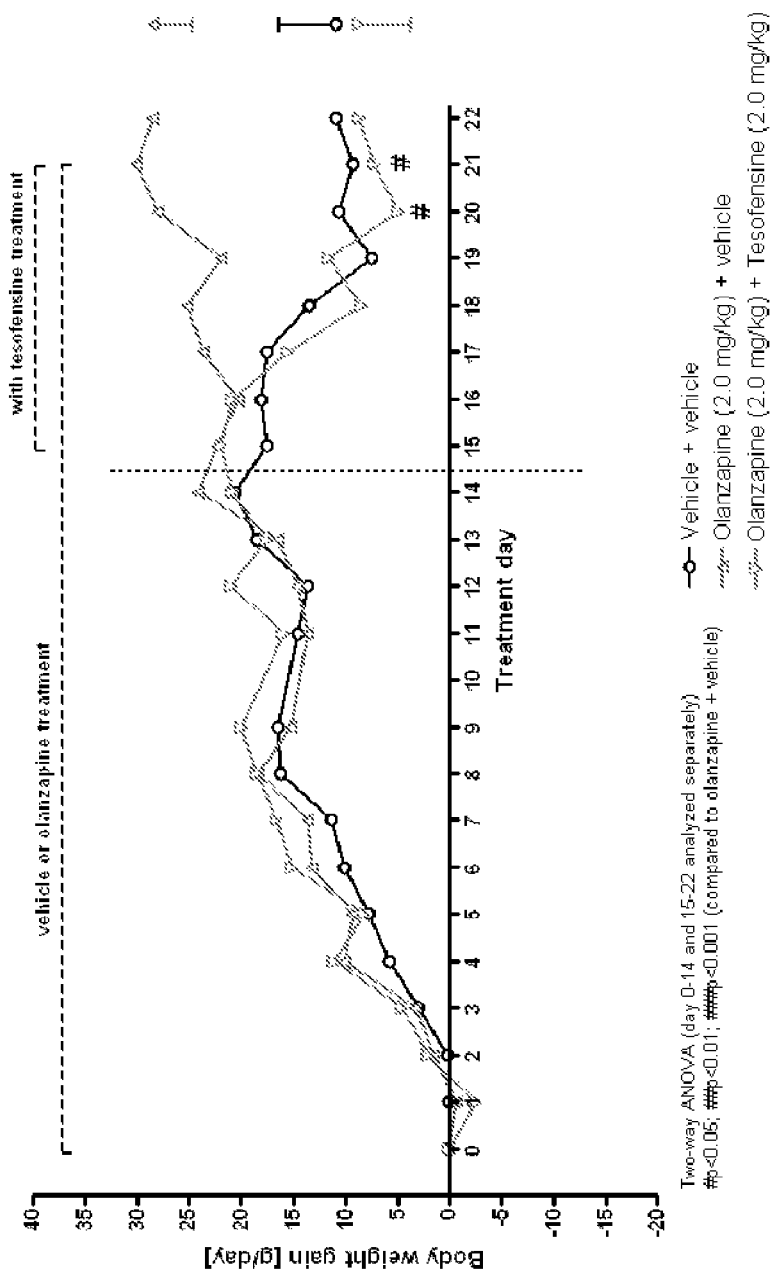
FIG. 1 shows body weight gain (g/day) in lean female SPRD rats during treatment days 0-22 (three weeks study), following treatment with vehicle; olanzapine (2.0 mg/kg)+vehicle; and olanzapine (2.0 mg/kg)+tesofensine (2.0 mg/kg)
Figure 2:
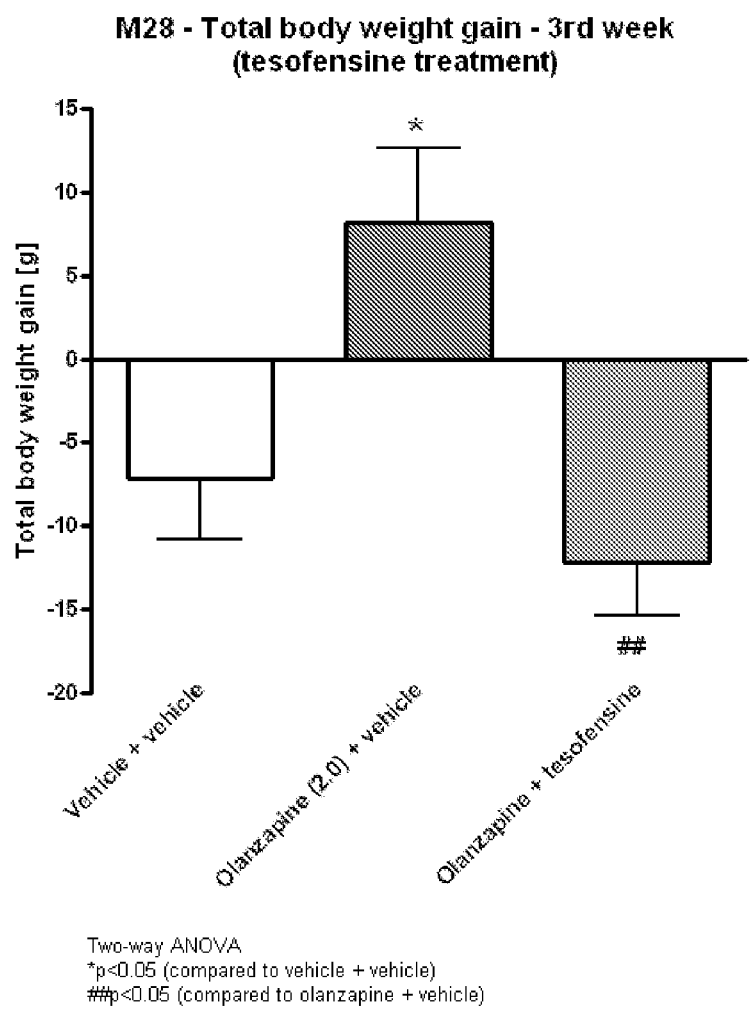
FIG. 2 shows total body weight gain (g) following treatment with vehicle; olanzapine (2.0 mg/kg)+vehicle; and olanzapine (2.0 mg/kg)+tesofensine (2.0 mg/kg).

In this example we determined the effect of tesofensine on weight gain induced by olanzapine in a rat model (three weeks study) of antipsychotic drug induced obesity. The results are presented in FIGS. 1-2.

Study Design

Female Sprague-Dawley (SPRD) rats were placed on 10% fat kcal futter. The rats were tagged subcutaneously with a microship in the neck and placed in an automatized food intake monitoring system. Upon habituation (5 days) the rats were allocated to either vehicle (2% lactic acid, n=12) or olanzapine (2.0 mg/kg, p.o., n=12) treatment for 14 consecutive days. On day 15, the vehicle group received vehicle (0.9% NaCl, s.c., n=6) or tesofensine (2.0 mg/kg, s.c., n=6) co-treatment, whereas the olanzapine-treated rats were assigned to either combined olanzapine+vehicle or olanzapine+tesofensine administration. Co-administration of vehicle or tesofensine continued for 7 days in total. Body weight and food intake was measured on a daily basis, and body weight gain and cumulative food intake was calculated. Data were evaluated using a two-way ANOVA with Bonferroni's post-hoc test (daily body weight gain and food intake) or a one-way ANOVA with Tukey's post-hoc test.

Results

Olanzapine-treated rats gained 5.7% (p<0.05) body weight during the three-week study, which was reflected by a significantly increased food intake (p<0.05) from day 11. Olanzepine-tesofensine co-treatment from day 15 and onwards completely prevented the body weight gain and hypophagic response to olanzapine.

CONCLUSION

Tesofensine prevents olanzapine-induced weight gain and hyperphagia in a rat model of antipsychotic drug induced obesity. This suggests that tesofensine may reduce risk factors for development of metabolic diseases, including diabetes, during antipsychotic drug treatment.

The invention claimed is:

1. A method of treatment or alleviation of an adverse effect arising from a previous antipsychotic treatment comprising
administering to a living animal body a combination of
a therapeutically effective amount of [(1R,2R,3S,5S)-3-(3,4-dichlorophenyl)-2-(ethoxymethyl)-8-azabicyclo[3.2.1]octane, or a pharmaceutically acceptable salt thereof; and
a therapeutically effective amount of an antipsychotic drug, or a pharmaceutically acceptable salt thereof;
wherein the combination is effective in treating or alleviating weight gain associated with the previous antipsychotic treatment.

2. The method of claim 1, wherein the antipsychotic drug combined with a therapeutically effective amount of [(1R,2R,3S,5S)-3-(3,4-dichlorophenyl)-2-(ethoxymethyl)-8-azabicyclo[3.2.1]octane, or a pharmaceutically acceptable salt thereof is olanzapine or a pharmaceutically acceptable salt thereof.

3. The method of claim 1, wherein the living animal body is a human.

4. The method of claim 1, wherein:
the adverse effect is weight gain;
the previous antipsychotic treatment is treatment with olanzapine or a pharmaceutically acceptable salt thereof; and
the living animal body is a human.

5. The method of claim 1, wherein the [(1R,2R,3S,5S)-3-(3,4-dichlorophenyl)-2-(ethoxymethyl)-8-azabicyclo[3.2.1]octane, or pharmaceutically acceptable salt thereof; and the antipsychotic drug, or pharmaceutically acceptable salt thereof, are administered simultaneously, sequentially, or separately.

6. The method of claim 1, wherein the previous antipsychotic treatment is treatment with amisulpride, aripiprazole, asenapine, bifeprunox, clozapine, iloperidone, melperone, olanzapine, paliperidone, quetiapine, risperidone, sertindole, ziprasidone, or zotepine, or a pharmaceutically acceptable salt thereof.

7. The method of claim 1, wherein the previous antipsychotic treatment is treatment with olanzapine.

8. The method of claim 1, wherein the previous antipsychotic treatment is treatment with clozapine.

9. The method of claim 6, wherein the antipsychotic drug combined with a therapeutically effective amount of [(1R,2R,3S,5S)-3-(3,4-dichlorophenyl)-2-(ethoxymethyl)-8-azabicyclo[3.2.1]octane, or a pharmaceutically acceptable salt thereof is amisulpride, aripiprazole, asenapine, bifeprunox, clozapine, iloperidone, melperone, olanzapine, paliperidone, quetiapine, risperidone, sertindole, ziprasidone, or zotepine, or a pharmaceutically acceptable salt thereof.

10. The method of claim 7, wherein the antipsychotic drug combined with a therapeutically effective amount of [(1R,2R,3S,5S)-3-(3,4-dichlorophenyl)-2-(ethoxymethyl)-8-azabicyclo[3.2.1]octane, or a pharmaceutically acceptable salt thereof is olanzapine or a pharmaceutically acceptable salt thereof.

11. The method of claim 8, wherein the antipsychotic drug combined with a therapeutically effective amount of [(1R,2R,3S,5S)-3-(3,4-dichlorophenyl)-2-(ethoxymethyl)-8-azabicyclo[3.2.1]octane, or a pharmaceutically acceptable salt thereof is clozapine or a pharmaceutically acceptable salt thereof.

* * * * *